US006331304B1

(12) United States Patent
Papadopoulou et al.

(10) Patent No.: US 6,331,304 B1
(45) **Date of Patent: *Dec. 18, 2001**

(54) MACROPHAGE-INFECTING PARASITES EXPRESSING A GRANULOCYTE MACROPHAGE COLONY STIMULATING FACTOR

(75) Inventors: Barbara Papadopoulou; Marc Ouellette; Martin Olivier, all of Quebec (CA)

(73) Assignee: Universite Laval, Sainte-Foy (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/713,768

(22) Filed: Sep. 13, 1996

(51) Int. Cl.$^7$ ............................ A61K 39/008; C12N 1/11
(52) U.S. Cl. ................... 424/269.1; 424/85.1; 435/258.3
(58) Field of Search ................................ 424/269.1, 85.1, 424/178.1; 536/23.1, 23.4, 23.5, 24.2; 435/320.1, 325, 69.5, 258.3; 530/350.1

(56) References Cited

FOREIGN PATENT DOCUMENTS

9506729 * 9/1995 (WO).

OTHER PUBLICATIONS

Moore et al (1994) J. Immunol. 152, 2930–2937.*
Wong et al (1985) Science 228, 810–815.*
Weiser et al (1987) J. Exp. Med., 166, 1436–1446.*
Laban et al (1990) Nature 343, 572–574.*

* cited by examiner

*Primary Examiner*—Gary L. Kunz
*Assistant Examiner*—Stephen Gucker
(74) *Attorney, Agent, or Firm*—Sim & McBurney

(57) ABSTRACT

Strains of Leishmanda and other macrophage-infecting parasites are provided which express the GM-CSF gene which are useful in treating hosts infected by the parasite and in protecting hosts against disease caused by infection of hosts by parasites. The parasites are reduced in their ability to infect or survive in macrophages and hence are attenuated. At least one gene of the parasite contributing to the virulence thereto may be functionally disabled. The attenuated strains may be used for administration to a host (a) to treat a host infected by Leishmania or (b) to confer protection against disease caused by a virulent Leishmania strain, or as a diagnostic reagent.

7 Claims, 7 Drawing Sheets

MACROPHAGE-INFECTING PARASITES EXPRESSING A GRANULOCYTE MACROPHAGE COLONY STIMULATING FACTOR

FIELD OF INVENTION

The present invention relates to the field of molecular immunobiology and in particular to immunogenic preparations including vaccines comprising attenuated

BACKGROUND OF INVENTION

Parasite infection is responsible for a number of human and animal diseases.

Parasitic protozoa of the order Kinetoplastidae are the causative agents of several tropical diseases including sleeping sickness by *Trypanosoma brucei*, Chagas by *Trypanosoma cruzi*, visceral (kala-azar) and cutaneous (oriental sore) Leishmaniasis by Leishmania donovani and *Leishmania major* respectively. In particular Leishmania protozoans are the causative agents of human leishmaniasis, which includes a spectrum of diseases ranging from self-healing skin ulcers to fatal visceral infections, Human leishmaniasis is caused by at Least thirteen different species and subspecies of parasites of the genus Leishmania. Leishmaniasis has been reported from about eighty countries and probably some 400,000 new cases occur each year. Recently the World Health Organization has reported 12 million people to be infected (ref. 1. Throughout this application various references are referred to in parenthesis to more fully describe the state of the art to which this invention pertains. Full bibliographic information for each citation is found at the end of the specification, immediately preceding the claims. The disclosure of these references are hereby incorporated by reference into the present disclosure. A listing of the references appears at the end of the disclosure).

Untreated visceral leishmaniasis is usually fatal and mucocutaneous leishmaniasis produces mutilation by destruction of the naso-oropharyngeal cavity and, in some cases, death.

In addition a major health problem has been created in areas of high infection when blood is collected for transfusion purposes. Since blood is a carrier of the parasites, blood from an infected individual may be unknowingly transferred to a healthy individual.

The Leishmania protozoans exist as extracellular flagellated promastigotes in the alimentary tract of the sandfly in the free-living state, and are transmitted to the mammalian host through the bite of the insect vector. Once introduced, the promastigotes are taken up by macrophages, rapidly differentiate into non-flagellated amastigotes and start to multiply within the phagolysosomal compartment, As the infected cells rupture, amastigotes suabsequently infect other macrophages giving rise to the various symptoms associated with leishmaniasis (refs 1 and 2).

Leishmaniasis is, therefore, a serious disease and various types of vaccines against the disease have been developed, including live parasites; frozen promastigotes from culture; sonicated promastigotes; gamma-irradiated live promastigotes; and forrmalin-killed promastigotes treated with glucan (reviewed in, for example ref. 3). However, none of these approaches have provided efficacious vaccines.

Healing and progression of leishmaniasis are linked to the dissimilar expansion of functionally distinct CD4+ lymphocyte responses separated on the basis of their cytokine potential (ref. 4). T helper type 1 (Th1) subset produces interferon (IFN)-, γ and interleukin (IL)-2 and leads to resistance to Leishmania infection, whereas Th2 cells producing IL-4, IL-5 and IL-10 confer susceptibility (ref. 5). In mammalian hosts, Leishmania 35 reside exclusively within mononuclear phagocytes, macrophages and mnonocytes. Cytokines can modulate macrophage differentiation by causing selective changes in macrophage gene expression, leading to alterations on macrophage functions (ref. 6). Macrophages, pre-incubated in vitro with cytokines prior to infection with Leishmania, acquire the capacity to kill the intracellular parasites (refs. 7 to il). Furthermore, cytokines such as IFN-γ, TNF-α, IL-12 and GM-CSF have been used in anti-leishmanial therapy in experimental models (refs. 12 to 17). Expression of the IFN-γgene has been performed in L. major trypanosomatids. When nude mice were infected with the IFN-γ expressing transfectant, the progression of the disease was considerably slower (ref. 17). The progression of the disease was not retarded in susceptible BALB/c mice however.

GM-CSF is a cytokine with multipontential hetnatopoietic function, stimulating the formation of granulocytes, macrophages, and eosinophils (ref. 18). It activates microphage tumoricidal activity (ref. 19), increases macrophage killing of *Trypanosorna cruzi* (ref. 20) and enhances in vitro killing of *L. donovani* within macrophages (ref. 8).

Differences on the effect of this cytokine have been reported between experimental visceral and cutaneous infections (ref. 27). Although in the *L. donovani* model, GM-CSF demonstrates a clear-cut leishmanicidal activity in vitro and in vivo (refs. 28), the results obtained with *L. major* are conflicting suggesting that GM-CSF may play a positive (refs. 29, 10, 6), neutral (refs. 30, 4) or negative (ref. 31) host defense role.

Parasitic infection of macrophages and, in particular, Leishmania infection may lead to serious disease. It would be advantageous to provide attenuated strains of Leishmania and methods of production thereof, for use as antigens in immunogenic preparations, including vaccines, and the generation of diagnostic reagents.

SUMMARY OF THE INVENTION

The present invention is directed towards novel strains of eishmania and other macrophage-infecting parasites, particularly attenuated strains. The novel macrophage-infecting parasites provided herein are useful for the preparation of immunogenic preparations including formulaations for the treatment of hosts infected by Leishmania and vaccines against disease caused by infection by a virulent Leishmania strain and as tools for the generation of immunological and diagnostic reagents.

In accordance with one aspect of the present invention, there is provided a macrophage-infecting parasite expressing a granulocyte macrophage colony stimulating factor (GM-CSF) gene. The parasite may be a strain of Leishmania, including a strain of Leishmania selected from the group consisting of *Leishmania donovani, Leishmania braziliensis, Leishmania tarentolae, Leishmania major, Leishmania mexicana, Leishmania tropica* and *Leishmania aethiopica.*

The parasite may be one which is reduced in the ability of the strain to infect or survive in macrophages and hence is attenuated. Further, at least one gene of the parasite contributing to virulence thereof may be functionally disabled. Additionally, the parasite may be further modified to express at least one additional cytokine which may be macrophage-activating.

The GM-CSF may be of murine origin or human origin. Expression of the GM-CSF gene from the parasite may be achieved by providing a plasmid into which the GM-CSF gene is inserted downstream of a promoter. For Leishmania, the intergenic region of the α-tubulin gene of *L. enriettii* may be used and the GM-CSF gene may be inserted into a Leishmania expression vector, which may be a plasmid.

In a further aspect, the present invention provides an immunogenic composition comprising an attenuated form of the parasites as provided herein.

The immnunogenic composition, for the parasite being a strain of Leishmania may be formulated for in vivo administration to a host, such as a primate, including humans, infected by Leishmania to treat such infection.

The immunogenic composition, for the parasite being a strain of Leishmania, may be formulated as a vaccine for in vivo administration to a host, such as a primate including humans, to confer protection against disease caused by a virulent strain of Leishmania, including *Leishmania donovani, Leishmania braziliensis, Leishmania tarentolae, Leishmania major, Leishmania mexicana, Leishmania tropica* and *Leishmania aethiopica.*

In an additional aspect, the invention provides a method of generating an immune response in a host, such as, a primate including humans, comprising administering thereto an immunoeffective amount of the immunogenic composition, as provided herein.

In yet an additional aspect, there is provided a method for producing a vaccine for protection against a disease caused by infection by a virulent strain of a macrophage-infecting parasite, including a virulent strain of Leishmania, including Leishmania donovani, Leishmania braziliensis, Leishmania tarentolae, *Leishmania mexicana, Leishmania tropica* and *Leishmania aethiopica*, and comprising administering the immunogenic composition as provided herein to a test host to determine an amount and frequency of administration thereof to confer protection against disease caused by infection by the Leishmania parasite and formulating the immunogenic composition in a form suitable for administration to a treated host, including humans, in accordance with said determined amount and frequency of administration.

Advantages of the present invention include the provision of safe and attenuated strains of Leishmania and other macrophage-infecting parasites for the preparation of immunogenic compositions including vaccines and for the generation of immunological and diagnostic reagents.

BRIEF DESCRIPTION OF THE DRAWINGS

FIG. 3A shows infection of murine macrophages. FIG. 3B shows infection of human marcrophages. The left graph of each Figure. corresponds to the percentage of infected macrophages and the right graph of each panel corresponds to thne total number of amastigotes in 100 macrophage cells with time. ■ *L. donovani*-pneo; ● *L. donovani*-mGM CSF; ▲ *L. donovani*-hGM CSF.

FIG. 4A shows the percentage of infected human macrophages with time. FIG. 4B shows the total number of amastigotes in 100 macrophage cells with time. ● *L. major*-pnec; ● *L. major*-hgM CSF; ○ *L. major*-hGM CSF R* representing the reverse orientation of the GM-CSF gene.

FIG. 5A shows the percentage of infected murine macrophages with time.

GENERAL DESCRIPTION OF THE INVENTION

Figure 1:
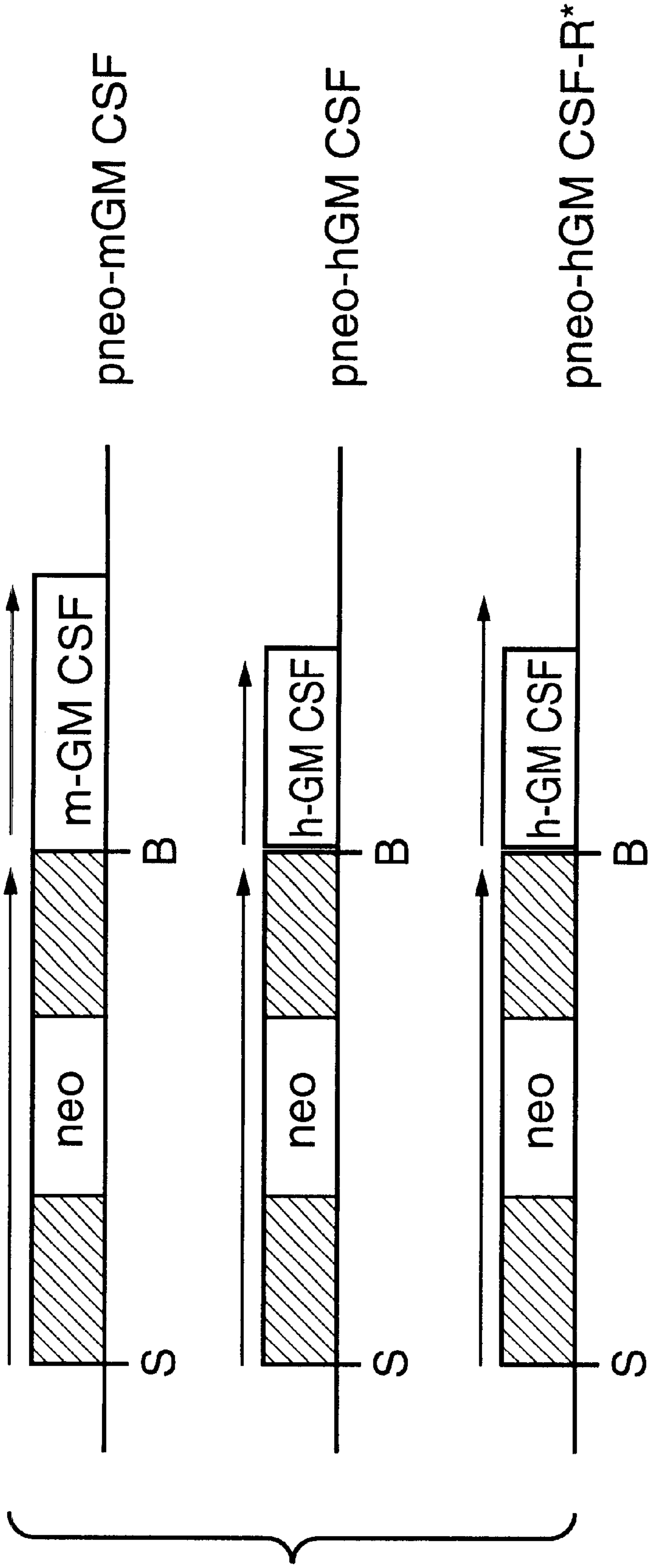
FIG. 1 shows the construction of Leishmania vectors expressing GM-CSF. Plasmids pneo-mGM 14 CSF and pneo-hGM CSF were made by inserting the murine and human GM-CSF genes, respectively downstream of the intergenic region of the α-tubulin gene of *L. enriettii* into pSP72-αneoα Leishmania expression vector as described in the Examples below. The cross-hatch box corresponds to the α-tubulin gene intergenic region (ref. 21). Arrows indicate the orientation of transcription of the genes present in the expression vectors.

Referring to FIG. 1, there is shown vectors for expression of the Granulocyte Macrophage Colony Stimulating Factor (GM-SP) in Leishmania.

Figure 2A:
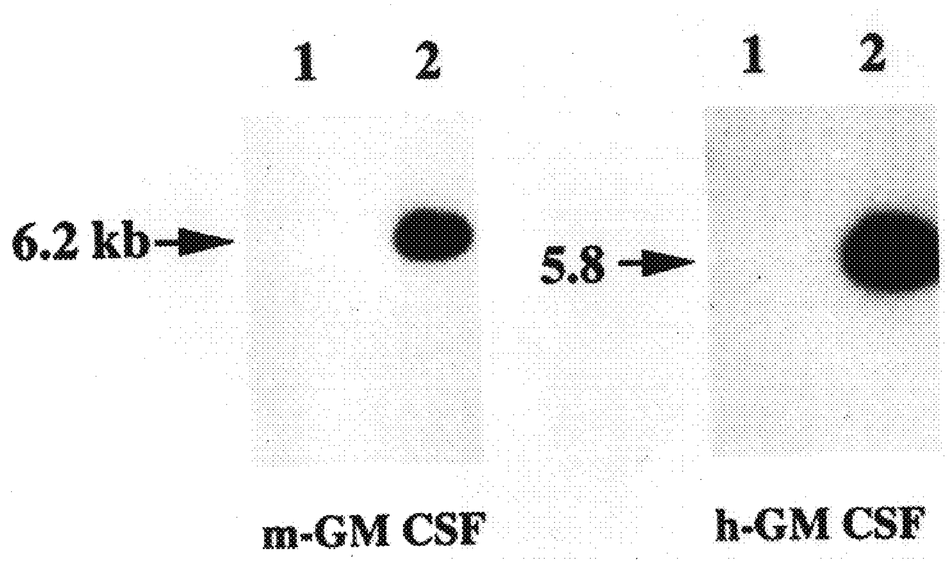
FIG. 2A is a southern blot of total genomic DNAs of *L. major* digested with BglII and hybridized to murine and human GM-CSF specific probes. Lane 1 corresponds to L. major-pneo and Lane 2 corresponds to *L. major* with either the murine or the human GM-CSF gene.
Figure 2B:
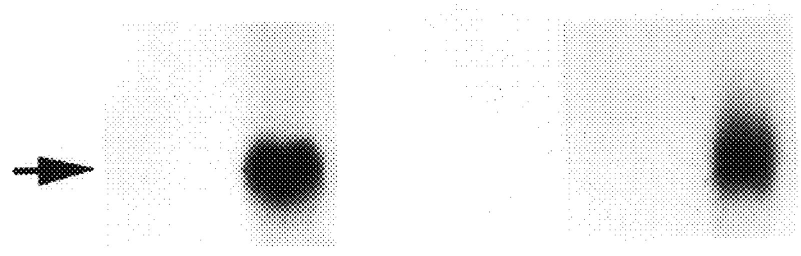
FIG. 2B shows mRNA expression in the L. major-GM CSF expressing cells. Northern blot of total Leishmania RNAs hybridized to the same probes as with panel A above. Lanes are as in A.

To express GM-CSF in Leishmania the 800 bp intergenic region of the α-tubulin gene of *L. enriettii* was subcloned upstream of either the murine or human GM-CSF genes. The α-tubulin intergenic region provides the necessary signals for trans-splicing that are required for correct maturation of transcripts in Leishmania (ref. 21). The same sequences were used for the expression of the neomycin phosphotransferase gene (neo) as part of an αneoα cassette cloned in vector pSP72 (FIG. 1). These vectors were transfected by electroporation into *L. major* and *L. donovani* strains and transfectants resistant to G418 were selected on SDM-1% agar plates. Genomic DNAs were isolated from selected clones, digested with BglII to linearize the GM-CSF expression vectors and analyzed by southern blot using GM-CSF specific probes either for the murine or the human genes. 5.8 kb and 6.2 kb fragments from the *L. major*-pneo-hGM CSF and pneo-mGM CSF transfectants, respectively were obtained as expected (FIG. 2A). Northern blot analysis of total *L. major* RNA showed that GM-CSF transcripts of the expected size for both the murine and the human genes were produced (FIG. 2B). Identical bands were also obtained for the *L. donovani*-GM CSF transfectants. The ability of *L. major*-and *L. donovani*-hGM CSF promastigotes to secrete CM-CSF was determined by direct ELISA assay. Leishmania cells were grown to stationary phase and the zupernatants harvested after centrifugation. As assessed by ELISA, Leishmania expressing the h-GMCSF gene were associated with detectable amounts of GM-CSF protein in the media. The concentration of h-GM CSF detected in culture media ranged from 2.8 to 6.2 ng/ml. GM-CSF expressing parasites can be maintained in culture as promastigotes for several months without any obvious effect on growth or morphology. Therefore, GM-CSF expression is not detrimental to Leishmania.

Figure 3A:
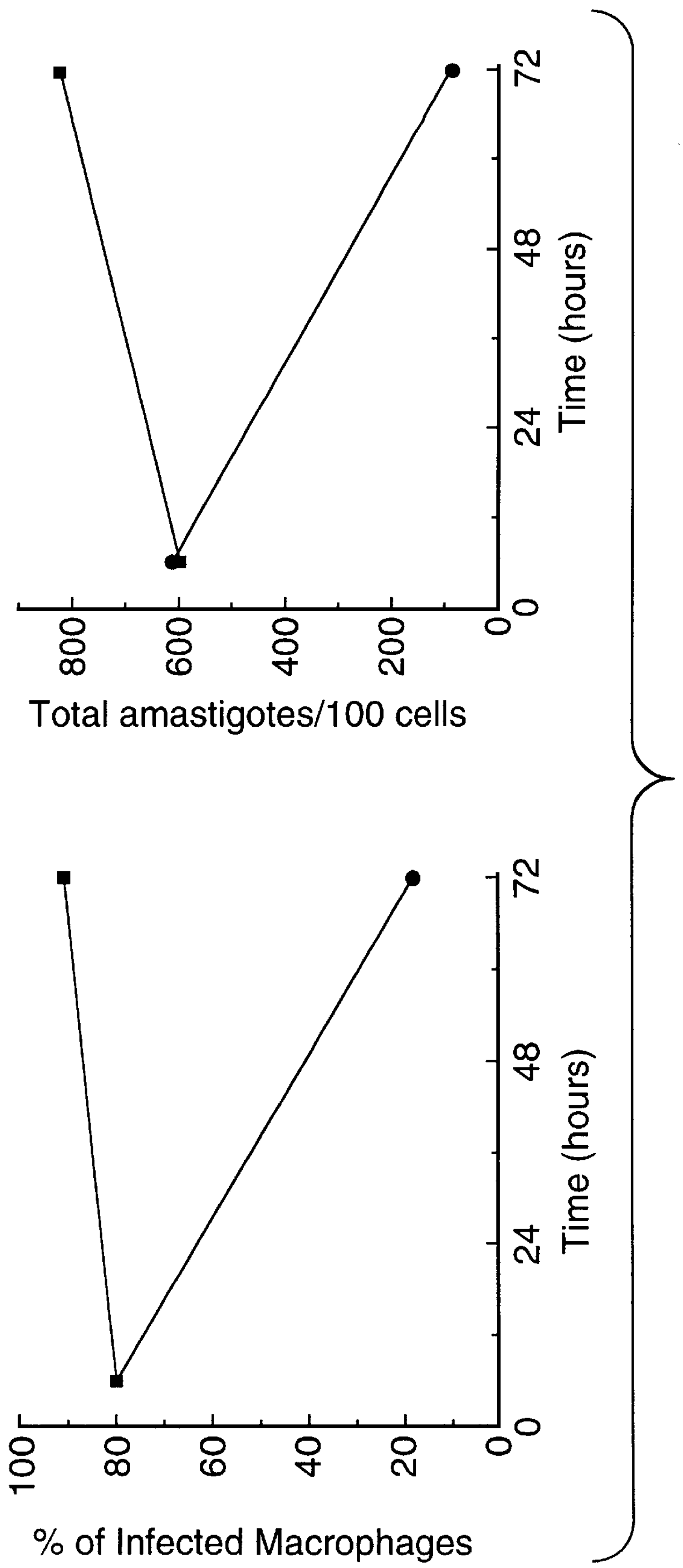
FIGS. 3A and 3B contain graphical representations of intramacrophage killing of *Leishmania donovani* amastigotes expressing the murine and human GM-CSF genes. *L. donovani* expressing either the murine or the human GM-CSF, gene were harvested from stationary phase and counted with the Neubauer improved counting chamrer. Murine macrophages from J774 cell line and human monocytes differentiated to macrophages ($5\times10^4$ cells/well) were incubated with stationary phase *L. donovani* parasites (20:1, parasite-to-cell ratio) for 6 hours. After this initial incubation, free parasites were washed and fresh media was added to the wells and incubated for 48 and 72 hours. At these fixed time point cell cultures were dried and stained with Diff Quick in order to determine the level of infection.
Figure 3B:
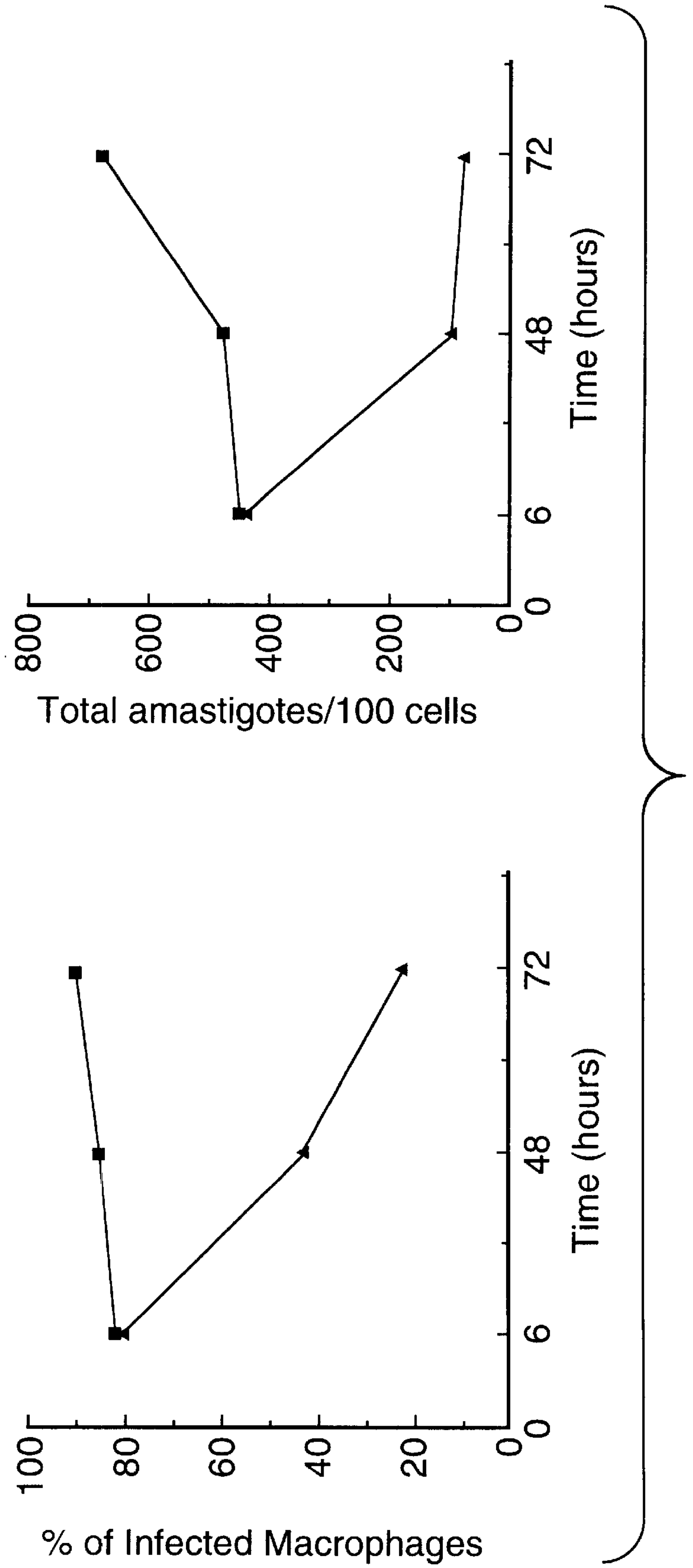
Figure 4A:
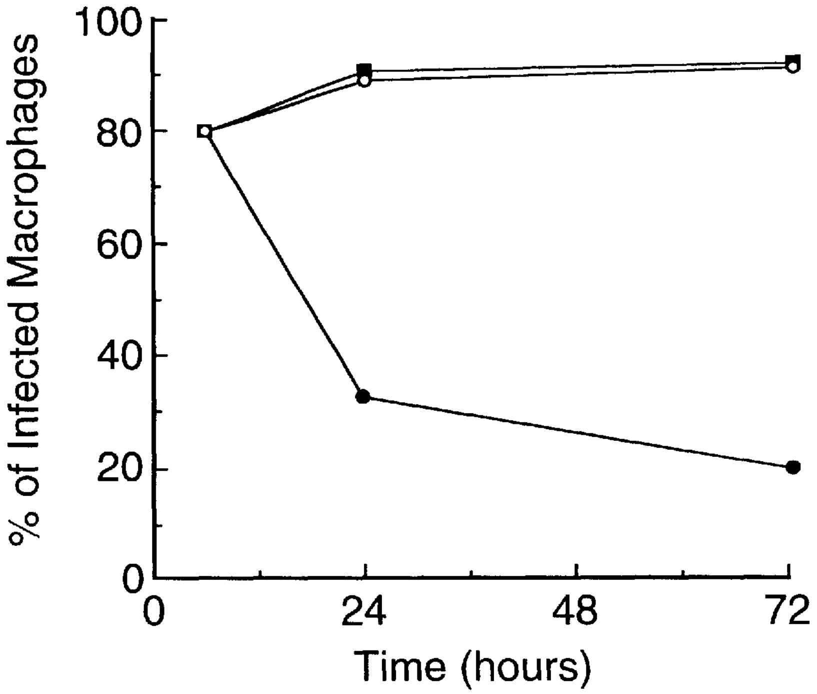
FIGS. 4A and 4B contain graphical representations of intracellular killing of *Leishmania major* amastigotes expressing the human GMCSF gene. Human monocytes differentiated into macrophages were infected by *L. major* expressing the hurman GM-CSF gene as described in FIGS. 3A and 3B.
Figure 4B:
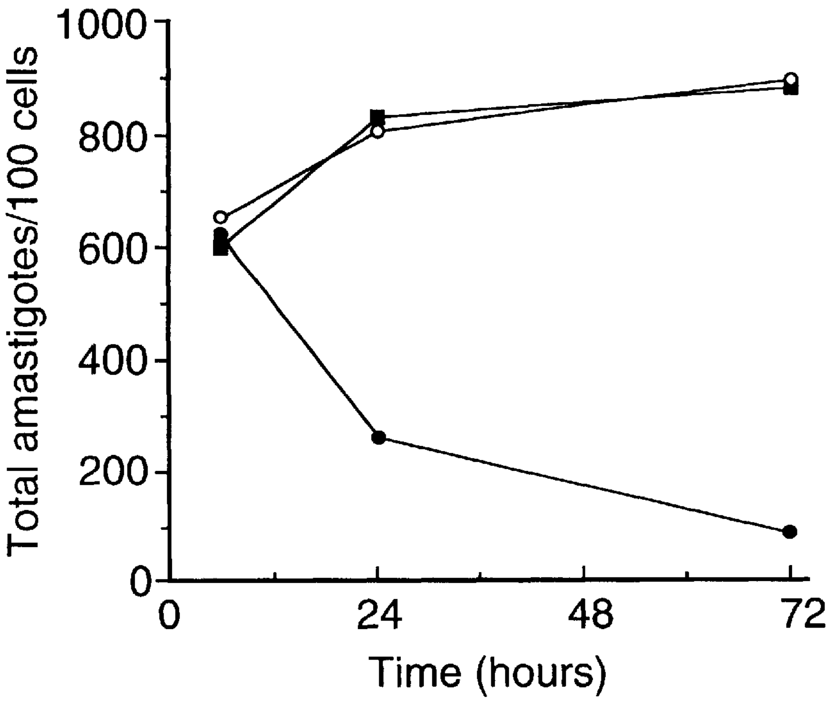
Figure 5A:
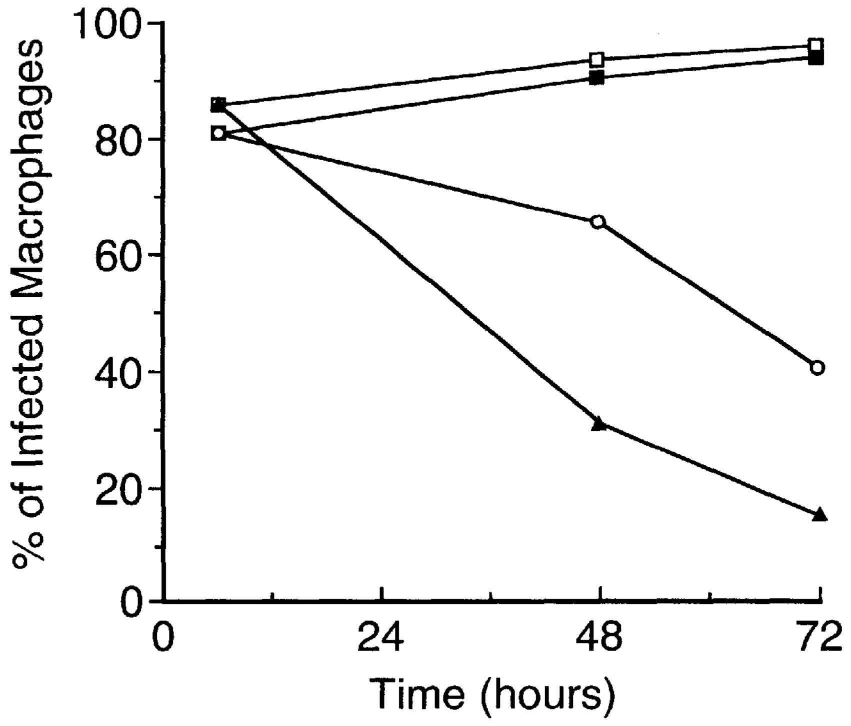
FIGS. 5A and B contain graphical representations of intracellular killing of *Leishmania major* amastigotes expressing the murine GM-CSF gene and reversion by an anti-GM CSF antibody. Murine macrophages were infected by *L. major* expressing the murine GM-CSF gene as described in FIGS. 3A and 3B.
Figure 5B:
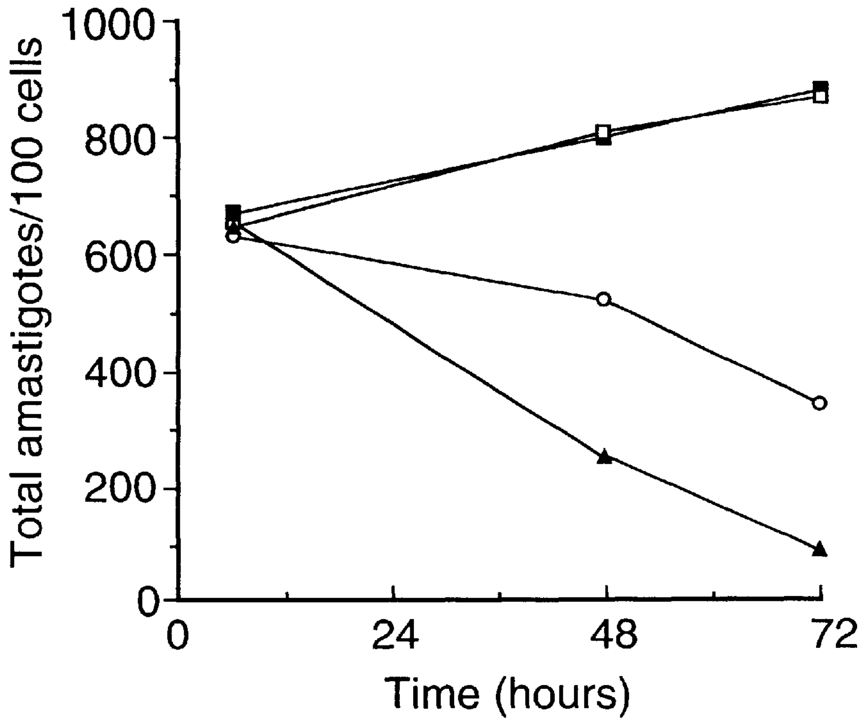
FIG. 5B shows the total number of amastigotes in 100 macrophage cells with time. ■ *L. major*-pneo; ▲ *L. major*-mGM CSF; □ *L. major*-pneo infection with macrophages pre-treated with a concentration of an anti-GM CSF antibody capable to neeutralize 50% of the GM-CSF activity; ○ *L. major*-mGM CSF infection with the same concentration of an anti-GMCSF antibody.

Referring to FIG. 3, there is shown the intramacrophage killing of Leishmania donovani expressing the murine and human GM-CSF genes. Phagocytes were infected with $10^6$ stationary phase Leishmania CSF and Leishmania-pneo control at a cell ratio of 1:20 for a period of 6 hours. The outcome of the infection in vitro was followed at 6, 24, 48, and 72 hours by microscopic examination. The intracellular survival of Leishmania amastigotes expressing GM-CSF significantly decreased inside both the murine and the human macrophages. More specifically, *L. donovani* amastigotes expressing either the murine or the human GM-CSF genes were eliminated 7 to 8-fold more rapidly inside macrophages than control cells 72 hours following infection (see FIG. 3A,B). Following the same infection period only 20% of macrophages were infected (FIGS. 3A, B). Similar results were observed with *L. major* parasites expressing GM-CSF. Indeed, 72 hours following infection only 18–20% of macrophages were infected compared to 92–95% for the control strain (FIGS. 4A and 5A). In addition, a 9-fold decrease was measured in the total amastigote number found inside either human or murine macrophages infected with *L. major*-GM-CSF expressing parasites compared to those infected with the control-neo strain (FIGS. 4B and 5B). The decrease in intracellular survival of Leishmania amastigotes expressing GM-CSF was a specific effect related to GM-CSF activity. Thus, murine macrophaaes were infected with Leishmania cells expressing either the human or the murine GM-CSF genes. Only parasites expressing the murine GM-CSF gene were eliminated inside macrcphages (FIG. 3A). Furthermore, a construct in which the hGM-CSF gene was cloned in the reverse orientation in respect to the α-tubulin intergenic region necessary for expression in Leishmania was not capable of inducing parasite elimination in infected macrophages (FIG. 4). Finally, by pre-treating murine macrophages with an anti-mGM CSF polyclonal antibody prior to infection, the anti-Leishmania effect of GM-CSF was significantly decreased (FIG. 5). Indeed, an antibody concentration capable of neutralizing 50% of the GM-CSF activity blocked more than 50% of the intra-macrophage elimination of *L. major*-mGY, CSF transfectants compared to the untreated cells (see FIG. 5). Similar results have been obtained using the *L. donovani* parasites. Thus GM-CSF expression greatly reduces the viability of amastigotes inside murine or human macrophages. GM-CSF induce parasite killing by activating macrophages to enhance $H_2O_2$ release (refs. 18, 20) or to produce more nitric oxide or to augment IFN-γ and IL-1 production (ref. 10). M-CSF, as IFN-γ, can increase production of the anti-leishmanial cytokine TNF-α (refs. 12, 13, 32, 33, 15) and some of its biological effects might be amplified through the release of this cytokine.

Figure 6:
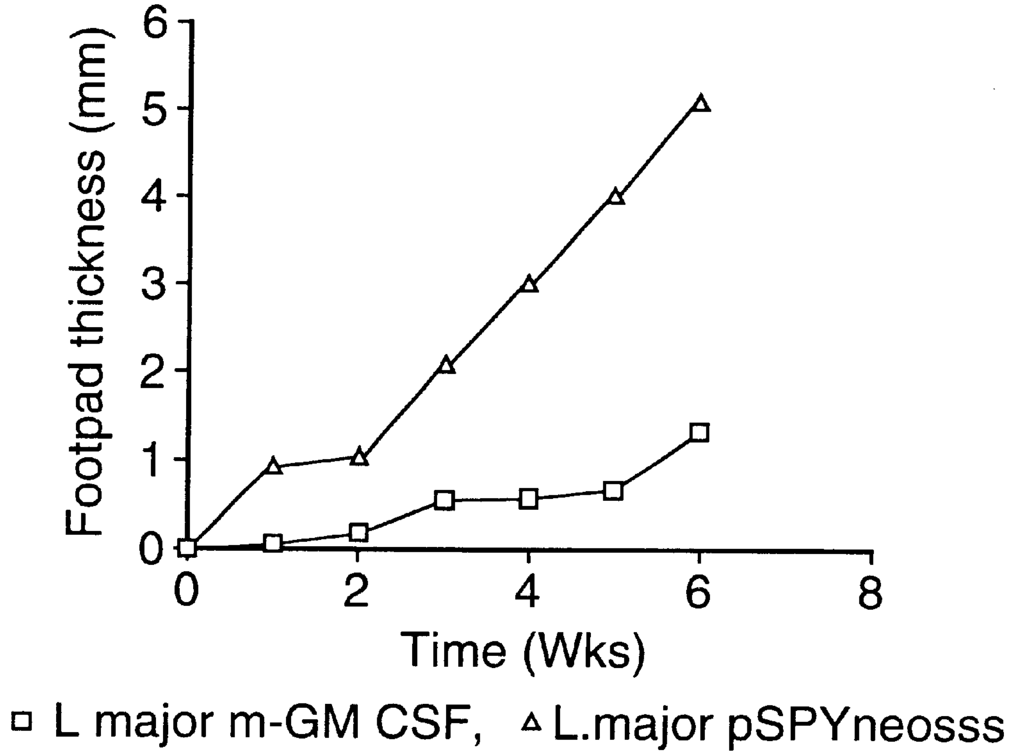
FIG. 6 is a graphical representation of the inability of *L. major* expressing GM-CSF to promote infection with BALB/C susceptible mice. $2\times10^2$ Leishmania pronascigotes expressing GM-CSF and also wild-type were injected into the footpad of eight mice per group. Infection was monitored by measuring the footpad lesion with a metric caliper over 6 weeks, ■ *L. major* m-GM CSF; ▲ *L. major* pSPYneosss mGM CSF.

Referring to FIG. 6, there is shown the inability of *L. major* expressing GM-CSF to promote infection of BALE/c susceptible mice. Two series of animals were inoculated into the footpad with either $2\times10^7$*L. major*-mGM CSF recombinant parasites (a clone) or with *L. major*-pSPYneo control strain. Eight mice were used for each group. The outcome of the infection of these mice was followed by weekly measurement of the footpad lesions. As shown in FIG. 6, after six weeks post-infection, a significant decrease in the development of cutaneous lesion was observed in animals inoculated with the GM-CSF expressing parasites compared to those infected with the neo control strain.

The Leishmania-GM-CSF expressing parasites provided herein provide means to create favorable immune responses in a host. Parasites expressing cytokines provide effective vaccines for leishmaniasis by mediating their own destruction while establishing protective Thi-mediated immunity.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry and immunology used but not explicitly described in the disclosure and these Examples are amply reported in the scientific literature and are well within the ability of those skilled in the art.

Example 1

This Example describes techniques of recombinant DNA.

Leishmania vector pneo-mGM CSF expressing the mrurine-GM-CSF gene was made as follows. A 1.2 kb KpnI-KpnI fragment isolated from plasmid pXMT2 containing the MGM-CSF gene and flanking sequences was filled in with T4 DNA polymerase (New England Biolabs) to create blunt ends and subcloned into the BamHI site of vector pSP72-αneoα filled in with Klenow DNA polymerase (New England Biolabs). Vector pSP72-αneoα was generated by subcloning the 2.6 kb BamHI-SmaI neo-cassette from pGEM3-neo (ref. 23) containing the neo gene flanked by the intergeniLc regions of the γ-tubulin gene of *L. enriettii* (ref. 21) into the BamHI-SmaI of pSP72 kPromega). The Leishmania construct to express the human GM-CSF gene was made by subcloning an 800 bp XhoI-XhoI fragment from vector PXMT1 containing the hGM-CSF gene and flanking sequences into the SalI site of pSP72-αneoα to yield pneo-hGM CSF. Construct pneo-hGM CSF R* corresponds to the reverse orientation of the human GM-CSF gene with respect to the αneoα cassette in such way that specific gene expression cannot occur. Total genomic DNA from Leishmania was prepared as described (ref. 26) digested with BglII resolved on 0.7% agarose gels and transferred to nylon membranes (Hybond-N, Amersham). Total RNAs from *L. major*-pneo and GM-CSF. transfectants were prepared using Trizol (Gibco BRL). Southern and Northern blots, hybridizations and washings were done following standard procedures. The GM-CSF probes used correspond to a 1.2 kb KpnI-KpnI fragment for the mGM-CSY gene and a 800 hp XhoI-XhoI fragment for the hGM-CSF gene.

Example 2

This Example describes the culturing and transfection of Leishmania.

*Leishmania major* MHOM/IL/67/JERICHO II; and *Leishmania donovani* donovani MHOM/IN/80/DD8 are WPAIR/WHO reference strains obtained from the ATCC. All strains were grown in SDM-79 medium (ref. 22) supplemented with 10% fetal bovine serum (FBS) (Multicell, Wisent Inc.) and 5 μg/ml of hemin. Approximately 15 μg of pneo-GM CSF vector DNA was used to transfect *L. donovani* and *L. major* cells by electroporation as described (refs. 23, 24). Transfectants were selected with 40 μg/ml of G-418 (Ceneticin, Gibco-BRL). Leishmania-GM CSF and control Leishmania-pneo transfectants were seeded at low concentration ($3\times10^4$ cells per culture dish) in 5 ml of SDM-79 medium. After 72 hours the cell density was obtained by measuring the absorbance at 600 nm using an automated microplate reader (Reader 510 from Organon Tecknika Inc., Austria). Murine macrophage cell line J774, obtained from ATCC, was cultured in Dulbecco's modified Eagle's medium (D-MEN, Gibco-BRL) supplemented with 10% FBS. Human peripheral blood monocytes were isolated from heparinized venous blood of normal donors by the Canadian Red Cross. Cells were centrifuged over Ficoll-Paque gradient (Pharmacia) as previously described (ref. 25). After several washes, cells were resuspended in RPMI 1640 medium (Gibco-BRL) containing 10% of human serum (Glbco-BRL). In order to differentiate monocytes into macrophages, $3\times10^6$ peripheral blood leukocytes were adhered and cultured for 5 days at 37° C. in 5% $CO_2$/95% air in a humidified atmosphere.

Example 3

This Example describes in vitro macrophage infection.

The capacity of Leishmania-GM CSF transfectants to infect murine and human macrophages in vitro was tested in comparison to control Leishmania-pneo as follows. Murine and human macrophages were seeded (200 μl per well, $5\times10^4$ cells/ml) into 8 wells chamber slides, and were infected with L. major-pneo and L. major-GM CSF at a parasite to cell ratio of 20:1 for a period of 6 hours. Following this incubation, non-engulfed parasites were removed by 3 to 5 washes with warm medium and chambers were replenished with 500 μl of fresh culture medium. The level of infection was determined at 6, 24, 48, and 72 hours by optical microscopy examination following Diff Quick staining of cell preparations.

Example 4

This Example describes the neutralization of GM-CSF activity.

Two hundred μl of J774 murine macrophages were incubated for 1 hour at 37° C. in the presence of 1 μg/ml of an anti-murine M-CSF polyclonal antibody (R&D Systems) prior to infection with Leishmania cells. Preincubated macrophages were then infected with *L major*-mGM CSF and wild-type parasites as described above in Example 3.

Example 5

This Example describes ELISA immunoassays.

Supernatants from *L. major*- and *L. donovani*-hGM CSF-containing parasites and from controls carrying only the neo vector were harvested by centrifugation following 5 days of culture with a reached density of $2\times10^7$ promastigotes/ml. Supernatants were assayed directlyl using a mAb ELISA kit (R&D Systems) as recommended by the manufacturers. Standard curves for quantification and comparison were generated using a recombinant hGM-CSF protein.

SUMMARY OF THE DISCLOSURE

In summary of the present disclosure, there is provided a macrophage-infecting parasite expressing a granulocyte macrophage stimulating factor (GM-CSF) gene for use as a vaccine against or treatment of a parasitic infection. in particular, the parasite may be a strain of Leishmania. Modifications are possible within the scope of the invention.

REFERENCES

1. WHO, Tropical Disease Report, 1989. pp. 85–92.
2. Turco, S. J. and Descoteaux, A., 1992. The lipophosphoglycan of Leishmania parasites. Annu. Rev. Microbiol. 46:65–94.
3. Modabber, F. 1989, Experiences with vaccines against cutaneous leishmaniasis: of men and mice. Parasitol. 98:849–860.
4. Coffman, R. et al. (1991) Immunol. Rev. 123:190–207.
5. Locksley, R. M. and Scott, P. (1991). Imnmunol. Today 12A: 58–A61.
6. Doherty, T. M and Coffman, R. L (1993) J. Immunol. 150: 5476–5483.
7. Oster, C. N. and Nacy, C. A. (1984) J. Immunol. 132: 1494.
8. Weiser, W. Y. et al. (1987) J. Exp. Med. 166: 1436–1446.
9. Hart, P. H. et al. (1988) J. Immunol. 141: 1516–1521.
10. Ho, J., Reed, S., wick, E., and Giordano, M. (1990) J. Infect. Dis. 162: 224–230.
11. Murray, H. W. (1994) Bailliere's Clin. Infect. Dis. 1: 237–246.
12. Titus, R. G., Sherry, B. and Ceramni, A. (1989) J. Exp. Med. 170: 2097–2104.
13. Liew, F. Y. et al. (1990a) Immunology 69:570.
14. Heinzel, F. P. et al. (1993) J. Exp. Med. 177: 1505–1509.
15. Tumang, M., Keogh, C., Moldawer, L., Helfgott, D., Hariprashad, J. and Murray, H. (1994) J. Immunol. 153; 768–775.
16. Murray, H. W. and Hariprashad, J. (1995) J. Exp. Med. 181; 387–391.
17. Murray, H. W. et al. (1995). J. Clin. Invest. 95: 1183–1192.
18. Silverstein, D. S. et al. (1986) J. Immunol. 137: 3290–3294.
19. Grabstein, K. H. et al. (1989) Science 232: 506–508.
20. Reed, S. G. et al. (1987) J. Exp. Med. 166: 1734–1746.
21. Laban, A. et al. (1990) Nature 343: 572
22. Brun, R. and Schonenberger, M. (1979) Acta Trop. 36: 289.
23. Green, S. J. et al. (1990) J. Immunol. 145:4290.
24. Muyombwe, A. et al. (1996) Exp. Parasitol. Submitted.
25. Oliver, M. et al. (1992). J. Immunol. 148: 1188–1196.

26. Bernards, A. et al. (1986). Cell, 27; 497–505.
27. Murray, H. W. (1994b) Parasitol. Today 10(6): 220–223,
28. Cervia, J. et al. (1993) Clin. Res. 41: 337.
29. Handman, E., and Burgess, A. W. (1979). J. Immunol. 122: 1134–1137.
30. Corcoran, L. M. et al. (1988) J. Parasitol. 74: 763–767.
21. Greil, J. et al. (1988) Eur. J. Immunol. 14: 1527–1537.
32. Liew, F. Y. et al. (1990b) J. Immunol. 145:4306.

What we claim is:

1. An immunogenic composition, comprising:

an attenuated form of a macrophage infecting parasite which is a strain of Leishmania and which is transformed by a plasmid containing a granulocyte macrophage stimulating factor (GM-CSF) gene and which parasite expresses GM-CSF.

2. The immunogenic composition of claim 1 wherein said parasite is a strain of Leishmania and said composition is formulated as a vaccine for in vivo administration to a host to elicit an immune response against disease caused by a virulent strain of Leishmania.

3. The immunogenic composition of claim 2 wherein the virulent strain is selected from the group consisting of *Leaishmania donovani, Leishmania braziliensis, Leishmania tarentolae, Leishmania major, Leishmania mexicana, Leishmania tropica* and *Leishmania aethiopica.*

4. The immunogenic composition of claim 2 wherein the host is a primate.

5. The immunogenic composition of claim 2 wherein the host is a human.

6. A method of generating an immune response in a host comprising administering thereto an immunoeffective amount of the immunogenic compositiorn of claim 1.

7. The composition of claim 1 wherein said strain of Leishmania is selected from the group consisting of *Leishmania donovani* and *Leishmania major* and said plasmid is selected from the group consisting of pneo-mGM CSF and pneo-hGM CSF.

* * * * *